United States Patent
Tepic et al.

(10) Patent No.: US 7,776,097 B2
(45) Date of Patent: Aug. 17, 2010

(54) DOUBLE SHELL IMPLANT FOR CEMENTLESS ANCHORAGE OF JOINT PROSTHESES

(75) Inventors: Slobodan Tepic, Zurich (CH); Henrik Malchau, Wellesley, MA (US)

(73) Assignee: Scyon Orthopaedics AG, AU-Waedenswill (CH)

( * ) Notice: Subject to any disclaimer, the term of this patent is extended or adjusted under 35 U.S.C. 154(b) by 0 days.

(21) Appl. No.: 11/547,518

(22) PCT Filed: Mar. 31, 2005

(86) PCT No.: PCT/EP2005/003380
§ 371 (c)(1),
(2), (4) Date: Oct. 2, 2006

(87) PCT Pub. No.: WO2005/094731
PCT Pub. Date: Oct. 13, 2005

(65) Prior Publication Data
US 2007/0208428 A1    Sep. 6, 2007

(30) Foreign Application Priority Data
Mar. 31, 2004   (EP)   .................................. 04007838

(51) Int. Cl.
*A61F 2/34*   (2006.01)
*A61F 2/36*   (2006.01)
*A61F 2/30*   (2006.01)
*A61F 2/28*   (2006.01)

(52) U.S. Cl. .............. 623/22.24; 623/22.32; 623/23.13; 623/23.39; 623/23.5

(58) Field of Classification Search .............. 623/19.13, 623/22.17–22.2, 22.24–22.29, 23.12–23.14, 623/23.43, 19.11, 19.12, 20.17, 20.22, 21.13, 623/21.16, 22.32, 22.33, 22.39, 23.11, 23.4, 623/23.5, 23.52, 23.54, 23.55

See application file for complete search history.

(56) References Cited

U.S. PATENT DOCUMENTS

| | | | |
|---|---|---|---|
| 3,905,777 A | | 9/1975 | Lacroix |
| 4,846,841 A | | 7/1989 | Oh |
| 5,133,769 A | * | 7/1992 | Wagner et al. ........... 623/23.13 |
| 5,147,407 A | | 9/1992 | Tager |
| 5,380,328 A | | 1/1995 | Morgan |
| 5,658,345 A | * | 8/1997 | Willi ....................... 623/22.26 |
| 5,879,398 A | | 3/1999 | Swarts et al. |
| 2003/0135281 A1 | | 7/2003 | Hanssen |

(Continued)

FOREIGN PATENT DOCUMENTS

CN    1135321 A    11/1996

(Continued)

*Primary Examiner*—David H. Willse
(74) *Attorney, Agent, or Firm*—Rothwell, Figg, Ernst & Manbeck, P.C.

(57) ABSTRACT

The invention solves the problem of anchoring a prosthetic component into compliant, cancellous bone by a thin, preferably pure titanium, or a titanium-based alloy, perforated, hence hydraulically open, shell (1, 13), spaced apart from the second, non-perforated shell (2, 14). In most applications, dictated by the anatomical site of insertion, shells are approximately hemispherical in form, connected to each other at the equator. The solid shell may contain a further, articulating component of the joint, e.g. a polymer or a ceramic insert, or it may serve that function itself. One or both components of a joint prosthesis can be anchored according to the invention.

19 Claims, 6 Drawing Sheets

U.S. PATENT DOCUMENTS

Figure 1:
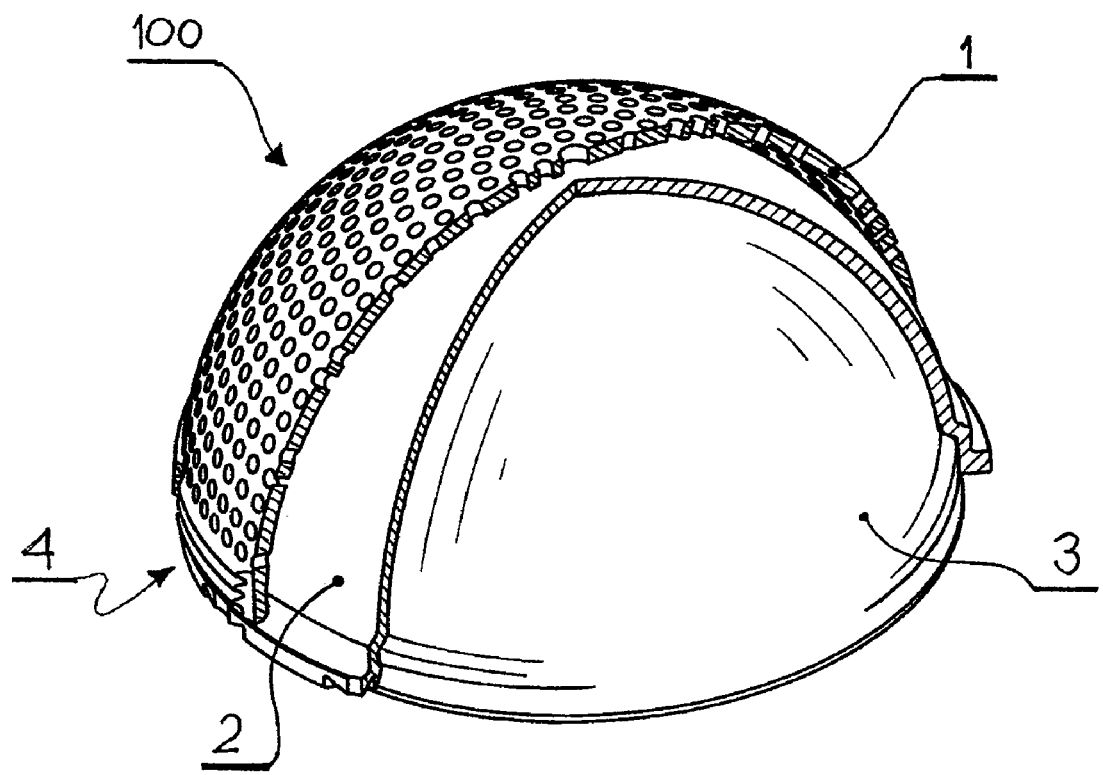

2006/0178750 A1 * 8/2006 Chieng .................... 623/22.27

FOREIGN PATENT DOCUMENTS

| | | | |
|---|---|---|---|
| CN | 1266670 A | * | 9/2000 |
| DE | 200 03 360 U1 | * | 6/2001 |
| EP | 0 230 006 A1 | | 7/1987 |
| EP | 420542 A1 | * | 4/1991 |
| EP | 0 430 831 A | | 6/1991 |
| JP | 4300539 A | | 10/1992 |

* cited by examiner

DOUBLE SHELL IMPLANT FOR CEMENTLESS ANCHORAGE OF JOINT PROSTHESES

CROSS REFERENCE TO RELATED APPLICATION

This application is a 35 USC § 371 National Phase Entry Application from PCT/EP2005/003380, filed Mar. 31, 2005, and designating the United States.

FIELD OF THE INVENTION

The invention relates to a bone anchoring component for joint prostheses, total, or partial, e.g. the acetabular cup of a total hip prosthesis, or a resurfacing prosthesis for the femoral head of the hip joint. It solves the problem of anchoring a prosthetic component into compliant, cancellous bone by a thin, preferably pure titanium, or a titanium-based alloy, perforated, hence hydraulically open, shell, spaced apart from the second, non-perforated shell. In most applications, dictated by the anatomical site of insertion, shells are approximately hemispherical in form, connected to each other at the equator. The solid shell may contain a further, articulating component of the joint, e.g. a polymer or a ceramic insert, or it may serve that function itself.

U.S. Pat. No. 3,905,777, FIG. 4B, discloses a composite implant shell with an inner and a perforated outer layer without any gap therebetween. EP 0 230 006 shows a flat bone implant with a core covered by a mesh spaced apart from the core surface by a plurality of spacers. U.S. Pat. No. 5,380,328 discloses a flat composite implant structure with two perforated titanium sheets sandwiching a porous membrane therebetween.

BACKGROUND

The main objective and the difficulty in design of a joint replacement is to provide for an immediate and indefinitely stable anchorage of the prosthetic components, serving as a kinematic pair to replace the natural articulation, which has lost its function through degenerative cartilage disease, for example. In some instances, one side of the natural joint is still in relatively good condition and a partial, or hemi-prosthesis can restore pain-free function.

In general, this objective requires solutions to two, partially coupled problems: (i) load-induced movement at bone-implant interfaces; (ii) stress shielding of the bone, particularly by conventional, stiff, solid metal, or metal-backed components. Bone cement in a Charnley-type total hip replacement (THR) accomplishes stability of the interface by an in situ polymerized interlock. In cases of stemmed components, such as conventional femoral components of a THR, anchored into tubular, cortical bone, bone cement also provides a compliant mantle, which can distribute the load more evenly and hence reduce the effects of stress shielding, while also reducing interface shear stresses and the risk of micromovement.

All of this is fine on a short, but less satisfactory on a long term basis—aseptic loosening is the most common reason for long term failure of THR's. The best efforts at analysis, as well as careful observation, suggest that fatigue failure of the cement mantle is a common and important component of the process leading to aseptic loosening. This has been the main driving force behind development of cementless THR, but clinical performance of all of the different types tested broadly enough and with sufficient follow-up, is still inferior to that of a well-designed, well-cemented THR (Malchau H, Herberts P, et al., Prognosis of Total Hip Replacement, Update and Validation of Results from the Swedish National Hip Arthroplasty Registry 1979-1998, Scientific Exhibition, AAOS, 2000, Orlando, USA). In most cases, cementless prostheses have replaced the soft cement mantle by more of a stiff metal added to an already stiff core element. This exacerbates both problems: a higher mismatch in stiffness leads to more pronounced stress shielding, but also to higher shear loads at interfaces and hence increased risk of micromotion.

The invention solves the problem of anchoring a prosthetic component into compliant, cancellous bone by a thin, preferably pure titanium, or a titanium-based alloy, perforated, hence hydraulically open, shell, spaced apart from the second, non-perforated shell. In most applications, dictated by the anatomical site of insertion, shells are approximately hemispherical in form, connected to each other at the equator. The solid shell may contain a further, articulating component of the joint, e.g. a polymer or a ceramic insert, or it may serve that function itself. One or both components of a joint prosthesis can be anchored according to the invention.

Acetabular Cup of a THR—A Preferred Embodiment of the Invention

Anchoring an acetabular cup into pelvic bones presents a difficult problem of providing for a fast integration by bony ingrowth, which requires mechanical stability, but also of avoiding large mismatches in compliance. Pelvic bones form a very compliant support structure for the acetabulum, whereby the cartilage layer covers a shell of hard, subchondral bone, backed by soft cancellous bone. Young's modulus of cancellous bone is on the order of 100 MPa—this is hundred times lower than that of dense cortical bone and thousand times lower than that of titanium. Even polymeric materials, such as UHMWPE, or PMMA-based, bone cement, are an order of magnitude stiffer.

In conventional cementless acetabular components, the subchondral shell is either completely removed in designs aiming for bone ingrowth, or partially retained in various threaded-type designs. The metal backing is usually a very stiff structure leading to a huge mismatch in compliance and seriously reducing the chances of a complete, long-lasting bony integration. Wire mesh-backed polymer acetabular cups developed by Sulzer Orthopaedics and Zimmer's metal foam backing (developed by Implex Corp.) exemplify the efforts to solve the problem of compliance mismatch.

In most cases, metal backing presents to the bone a textured surface, sometimes with interconnected pores running some depth into the material, but ending in closed, dead-end holes. Our preoccupation with the role of convective transports in bone growth and remodeling has led us to propose the concept of hydraulically open implants.

A solid, inner shell of a double-shelled metal-backing for the polyethylene (typically ultra high molecular weight polyethylene, UHMWPE) insert is suspended within a densely perforated outer shell, leaving about a millimeter of free space between the inner wall of the outer shell and the outer wall of the inner shell, i.e. bone is free to grow past the outer, perforated shell into this space. Bony ingrowth is accelerated by the convective fluid currents, set in motion by the cyclic pressure gradients caused by the physiological loading of the bone. Moreover, elasticity of the construction will lead to pumping of the fluid in and out of the bony bed and in and out of the perforated shell under dynamic loading of the hip. This is the main functional distinction over the perforated, cylindrical implants developed by Sutter, mostly for dental (Vuillemin T, Raveh J, Sutter F, Mandibular Reconstruction with the Titanium Hollow Screw Reconstruction Plate (THORP) System: Evaluation of 62 Cases, Plast Reconstr Surg, 82(5):804-14, 1988), but also for orthopaedic applications (WO 85/02535). In the present invention, fluid convection increases mass transport of important bone growth promoting factors emanating from the extant cancellous bone surrounding the implant.

The surface of the outer, perforated shell can further be treated by the methods known to enhance integration, e.g. rough blasting, or plasma coating by titanium or hydroxyapatite. This can improve so-called micro-interlock.

For improved press fit for the initial stabilization, the outer shell can also incorporate small protrusions running circumferentially just below the "equator". The "pole" of the shell can be slightly flattened to avoid the cups bottoming out at the "pole" without a full engagement at the "equator". These additional features are known in the art of acetabular cup design and have shown their clinical benefits.

DETAILED DESCRIPTION OF THE DOUBLE-SHELL ACETABULAR CUP FOR THR

List of Figures:

FIG. 1. A perspective view of the acetabular cup, from the back side, with partially cutout sections of the two shells.

Figure 2:
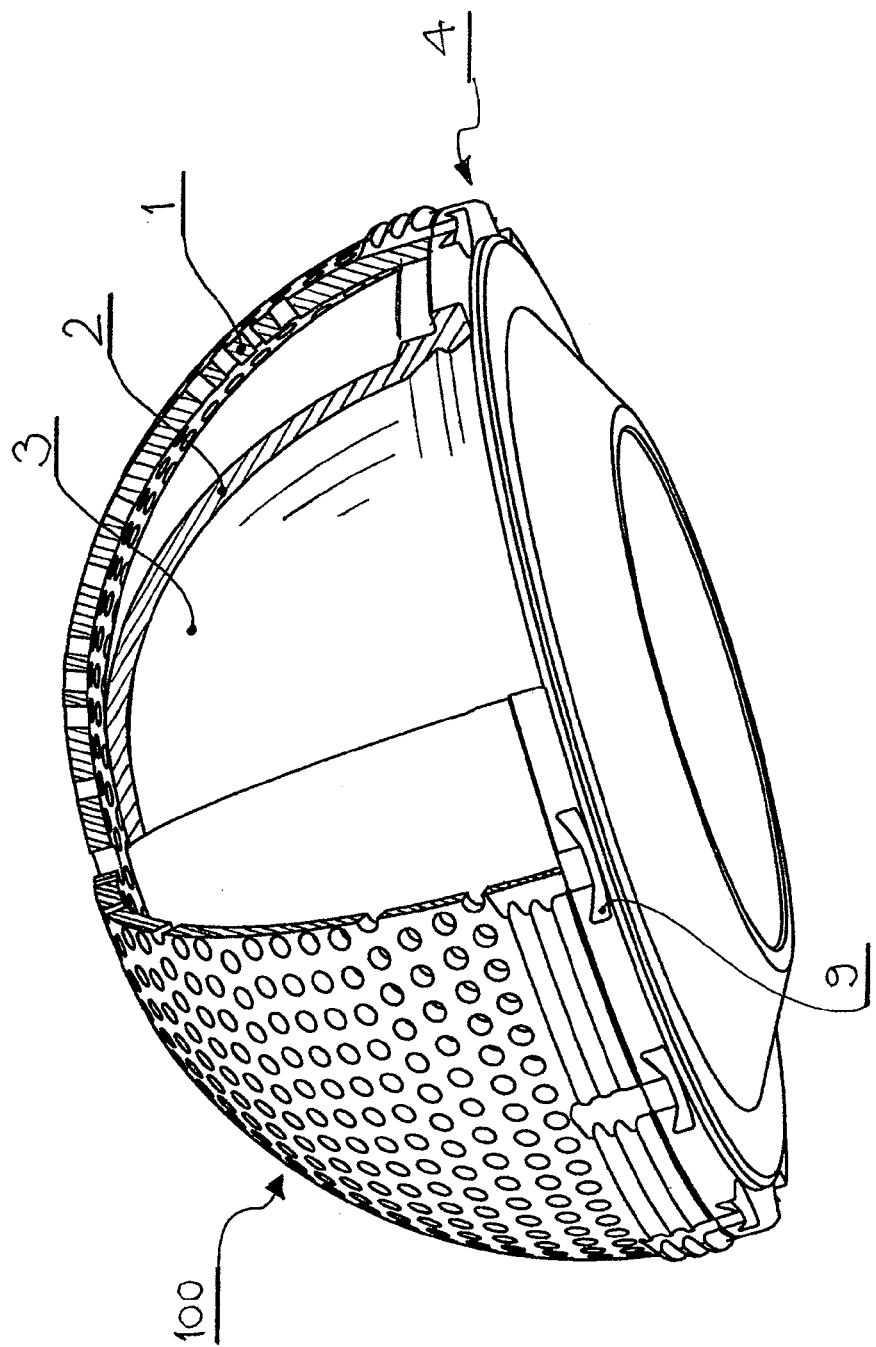

FIG. 2. A perspective view of the acetabular cup, from the front side.

Figure 3:
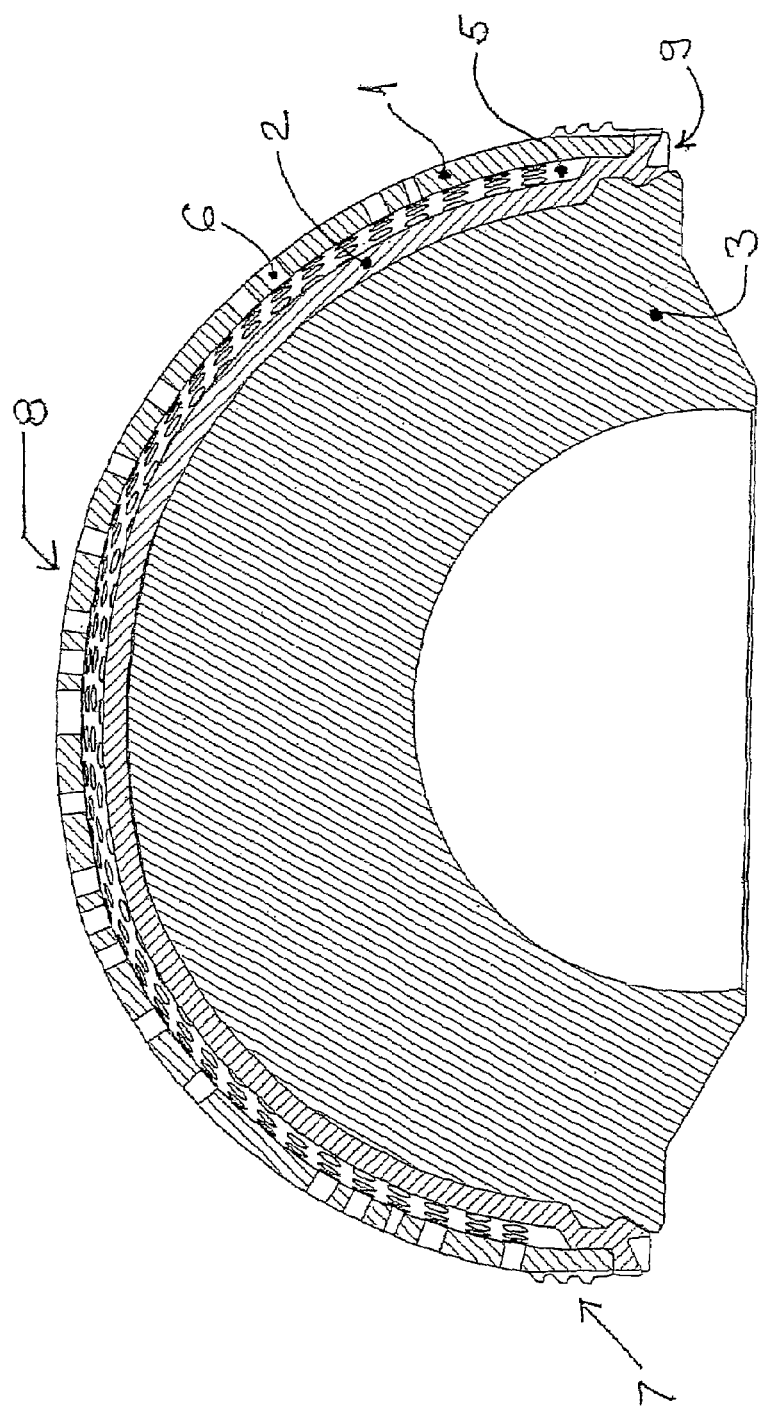

FIG. 3. Cross sectional view of the acetabular cup.

Figure 4:
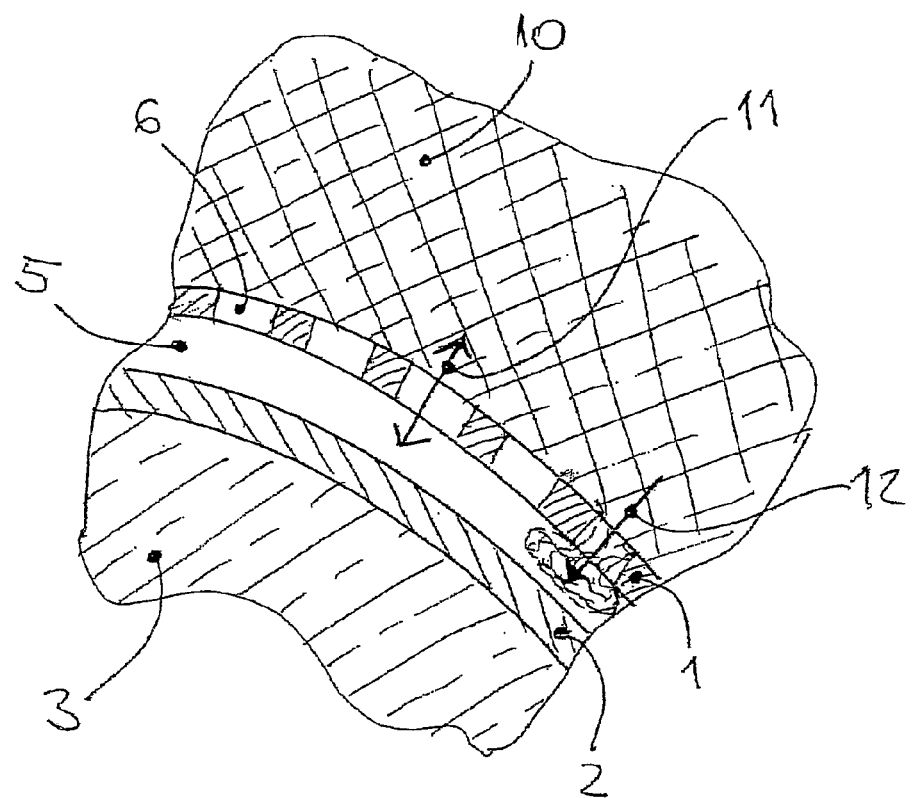

FIG. 4. Cross sectional view of the shells facing and being ingrown by the bone.

Figure 5:
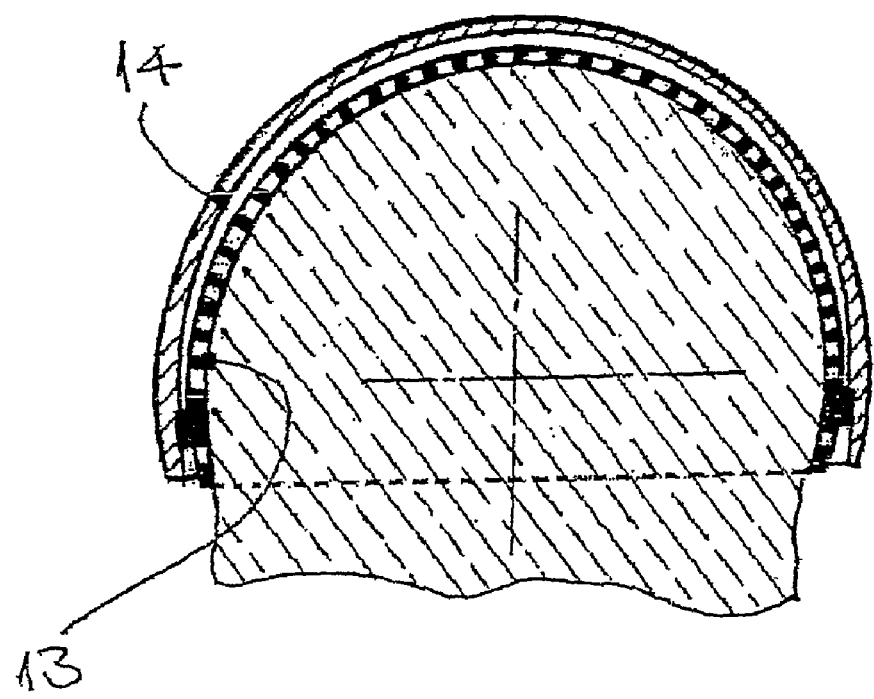

FIG. 5. Cross sectional view of a femoral head resurfacing prosthesis.

Figure 6:
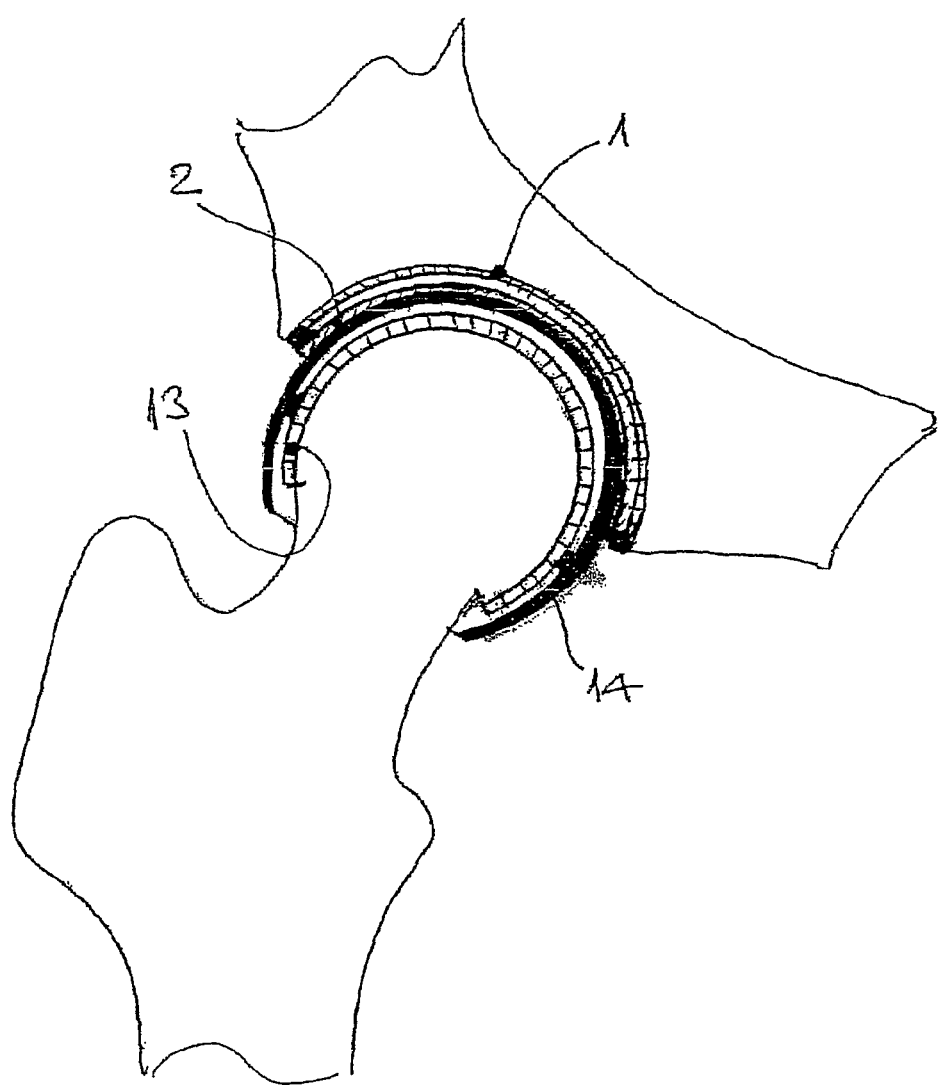

FIG. 6. Total hip prosthesis with both components anchored according to the invention.

The outer, bone-facing shell, 1, of the acetabular cup, 100, FIG. 1, is densely perforated and connected to the inner, non-perforated, shell, 2 at the equatorial aspect, 4. This can be accomplished by a press fit and/or by welding of the two components. When assembled, the two shells should be spaced apart by a gap, 5, FIG. 3, which will allow bone to freely grow past the outer shell, 1, through the perforations, 6. Typical dimensions, dictated by the mechanical requirements for machinability and strength, by economy of production, and by interfacing to cancellous bone with its typical metric, are one millimeter for the thickness of both the outer and the inner shell, one millimeter for the gap between the two shells and one millimeter for the diameter of the perforations. More particularly, the thickness of the perforated bone facing shell, 1, is in the range from 0.7 to 1.5 mm and the ratio of the thickness of the perforated bone facing shell to the perforation diameter is between 0.5 and 2. The width of the gap, 5, between the two spaced apart shells is in the range of 0.5 mm to 2 mm, preferably approximately 1 mm. These figures, of course, are only for the basic orientation of scaling and need to be appropriately adjusted to the size of the acetabulum. For example, for a 54 mm diameter cup, the final dimensions chosen were 1.2 mm for the thickness of both shells, 1 mm for the gap, 1.2 mm for the diameter of the perforations and 2 mm for hole spacing.

Both, the outer perforated shell, 1, and the inner, non-perforated shell, 2, are preferably produced from pure titanium. Titanium-based alloys may also be used where strength of the shell may be an issue. Typically produced from polyethylene (UHMWPE), the liner, 3, of the cup is inserted into the inner shell, 2, and here, again, preferably by a press-fit at the equatorial aspect, 4, FIG. 1. Optionally, the polyethylene liner may support the secondary, ceramic liner used for ceramic-ceramic joint pairs. The liners allow for low friction articulation against the head of the femoral component, usually produced from a chrome based alloy or a ceramic.

Rib protrusions, 7, FIG. 3, at the equatorial aspect of the cup may be used for added mechanical stability when the cup is press-fitted into reamed-out acetabulum. Polar aspect of the cup, 8, should preferably be somewhat flattened to avoid bottoming out of the cup—most commonly used reamers are hemispherical and if the cup were also a full hemisphere, the fit at the equator could be compromised.

Recesses, 9, at the periphery of the cup are to accommodate heads of the auxiliary screws should the need arise to use them—this may happen in a poorly formed or deformed acatabulum, preventing a solid press fit at the equator. Screws would then be placed just tangentially to the cup, with their suitably shaped heads catching the rim of the cup.

FIG. 4 is a schematic representation of the double shell implant facing the cancellous bony bed, 10. Under dynamic loading, as the outer, perforated shell, 1, pushes onto extant bone, 10, fluid, permeating all of the bone, is forced out of and then imbibed back into bone, as indicated by arrow 11, transporting bone growth stimulating substances from the bone, through the perforations, 6, into the gap, 5, separating the shells, 1 and 2. This leads to rapid bony ingrowth of the outer shell, 1, as indicated by arrow 12. Yet the inner, non-perforated shell, 2, separates the UHMWPE liner, 3, from making any contact with the newly formed bone. In mechanical terms, the ingrown outer shell mimics the removed subchondral bone of the natural acatabulum, without overt stress shielding of the supporting cancellous bone.

Femoral Head Resurfacing Prosthesis

By reversing the order, i.e. by placing the perforated, bone-facing shell, 13, inside a non-perforated one, 14, the same principles of fixation can be employed for resurfacing the femoral head, FIG. 5. Indeed, stress shielding here has been a serious limitation of the use of this minimally invasive technique, since all of the known resurfacing cups are solid, rigid implants, which are either cemented over the reamed-down femoral head, or press-fitted for cementless fixation.

In this case, the outer shell, 14, is preferably produced from a chrome-based alloy, or from a titanium alloy, hard coated with e.g. titanium nitride, or ion-implanted for increased wear resistance.

In yet another embodiment of the invention, both components of the prosthesis can be anchored by the use of the double shell concept, FIG. 6.

The invention claimed is:

1. A prosthetic component for cementless integration into bone comprising two, spaced apart, shells (1, 2; 13, 14), wherein a bone facing shell (1; 13) is perforated to allow for rapid bony ingrowth and wherein the perforated bone facing shell (1) and the other shell (2) are fitted into each other, wherein the spaced apart shells (1, 2) contact each other only at circumferential edges thereof while a continuous gap (5) left between the spaced apart shells (1, 2) freely extends in the area surrounded by the circumferential edges of the shells (1, 2; 13, 14) in any direction for bony ingrowth, wherein opposite pairs of circumferential surfaces and opposite pairs of radially extending surfaces at the respective circumferential edges of the two shells contact each other in each pair defining a constant width of the gap in any direction; wherein the thickness of the perforated bone facing shell is in the range from 0.7 to 1.5 mm; and wherein the ratio of the thickness of the perforated bone facing shell to the perforation diameter is between 0.5 and 2.

2. The prosthetic component according to claim 1 wherein the shells (1, 2) are made from titanium or a titanium-based alloy.

3. The prosthetic component according to claim 1, wherein the perforated bone facing shell (1) is made of a solid material and is self supporting in the area surrounded by the circumference edge thereof.

4. The prosthetic component according to claim 1 wherein the spaced apart shells (1, 2) are formed as concentrical cups.

5. The prosthetic component according to claim 1, wherein the perforated bone facing shell (1) is made of a perforated single sheet material.

6. The prosthetic component according to claim 1, wherein the center to center distance between adjacent perforations (6) is greater than the perforation diameter.

7. The prosthetic component according to claim 6, wherein the center to center distance between adjacent perforations is greater than the perforation diameter by a factor of 1.2 to 2.

8. The prosthetic component according to claim 6, wherein the center to center distance between adjacent perforations is greater than the perforation diameter by a factor of about 1.7.

9. The prosthetic component according to claim 1, wherein the ratio of the thickness of the perforated bone facing shell to the perforation diameter is about 1.

10. A joint prosthesis comprising two joint components, wherein at least one of the joint components is anchored with a prosthetic component comprising two, spaced apart, shells (1, 2; 13, 14), wherein a bone facing shell (1; 13) is perforated to allow for rapid bony ingrowth and wherein the perforated bone facing shell (1) and the other shell (2) are fitted into each other, wherein the spaced apart shells (1, 2) contact each other only at circumferential edges thereof while a continuous gap (5) left between the spaced apart shells (1, 2) freely extends in the area surrounded by the circumferential edges of the shells (1, 2; 13, 14) in any direction for bony ingrowth, wherein opposite pairs of circumferential surfaces and opposite pairs of radially extending surfaces at the respective circumferential edges of the two shells contact each other in each pair defining a constant width of the gap in any direction; wherein the thickness of the perforated bone facing shell is in the range from 0.7 to 1.5 mm; and wherein the ratio of the thickness of the perforated bone facing shell to the perforation diameter is between 0.5 and 2.

11. The joint prosthesis of claim 10, wherein both of the joint components are anchored with a respective said prosthetic component.

12. An acetabular cup for a total hip prosthesis, comprising two, spaced apart, shells (1, 2; 13, 14), wherein a bone facing shell (1; 13) is perforated to allow for rapid bony ingrowth and wherein the perforated bone facing shell (1) and the other shell (2) are fitted into each other, wherein the spaced apart shells (1, 2) contact each other only at circumferential edges thereof while a continuous gap (5) left between the spaced apart shells (1, 2) freely extends in the area surrounded by the circumferential edges of the shells (1, 2; 13, 14) in any direction for bony ingrowth, wherein opposite pairs of circumferential surfaces and opposite pairs of radially extending surfaces at the respective circumferential edges of the two shells contact each other in each pair defining a constant width of the gap in any direction; wherein the thickness of the perforated bone facing shell is in the range from 0.7 to 1.5 mm; and wherein the ratio of the thickness of the perforated bone facing shell to the perforation diameter is between 0.5 and 2.

13. The acetabular cup according to claim 12, wherein the width of the gap (5) between the two spaced apart shells is in the range from 0.5 to 2 mm.

14. The acetabular cup according to claim 13, wherein the width of the gap (5) between the two spaced apart shells is approximately 1 mm.

15. The acetabular cup according to claim 12, wherein the other shell (2) contains a liner (3) for low friction articulation against the femoral component of the total hip prosthesis.

16. The acetabular cup according to claim 12, wherein the shells (1, 2) are made from titanium or a titanium-based alloy.

17. The acetabular cup according to claim 12, wherein the outer, perforated shell (1) is approximately hemispherically shaped and is connected to the other shell (2) at the equatorial aspects (4) thereof extending along the respective circumferential edges of the two shells (1, 2).

18. A resurfacing prosthesis for a femoral head comprising two, spaced apart, shells (1, 2; 13, 14), wherein a bone facing shell (1; 13) is perforated to allow for rapid bony ingrowth and wherein the perforated bone facing shell (1) and the other shell (2) are fitted into each other, wherein the spaced apart shells (1, 2) contact each other only at circumferential edges thereof while a continuous gap (5) left between the spaced apart shells (1, 2) freely extends in the area surrounded by the circumferential edges of the shells (1, 2; 13, 14) in any direction for bony ingrowth, wherein opposite pairs of circumferential surfaces and opposite pairs of radially extending surfaces at the respective circumferential edges of the two shells contact each other in each pair defining a constant width of the gap in any direction; wherein the thickness of the perforated bone facing shell is in the range from 0.7 to 1.5 mm; and wherein the ratio of the thickness of the perforated bone facing shell to the perforation diameter is between 0.5 and 2.

19. The resurfacing prosthesis according to claim 18, wherein the two shells are arranged so that the perforated, bone facing one (13) is inside the other shell (14), which articulates against an acetabulum, the two shells being connected at equatorial aspects (4) thereof extending along the respective circumferential edges of the two shells (13, 14).

\* \* \* \* \*